US006679905B2

(12) United States Patent
Peetros et al.

(10) Patent No.: US 6,679,905 B2
(45) Date of Patent: Jan. 20, 2004

(54) MODULAR DROP MECHANISM FOR CHIROPRACTIC TABLE

(75) Inventors: Christopher H. Peetros, Fredericksburg, PA (US); Blake Pruett, Hixson, TN (US)

(73) Assignee: Encore Medical Asset Corporation, Austin, TX (US)

( * ) Notice: Subject to any disclaimer, the term of this patent is extended or adjusted under 35 U.S.C. 154(b) by 48 days.

(21) Appl. No.: 09/795,164

(22) Filed: Feb. 27, 2001

(65) Prior Publication Data

US 2002/0120293 A1 Aug. 29, 2002

(51) Int. Cl.[7] .................................................. A61F 5/00

(52) U.S. Cl. ....................................... 606/241; 606/243

(58) Field of Search ................................ 606/240, 241, 606/242, 243, 244, 245; 128/845

(56) References Cited

U.S. PATENT DOCUMENTS

| | | | |
|---|---|---|---|
| 4,245,626 A | | 1/1981 | Paolino |
| 4,271,830 A | * | 6/1981 | Moon |
| 4,523,581 A | | 6/1985 | Ekholm |
| 4,856,497 A | * | 8/1989 | Westphal |
| 4,903,689 A | | 2/1990 | Lannertone |
| 5,423,861 A | * | 6/1995 | Kelley |
| 5,954,750 A | * | 9/1999 | Steffensmeier |
| 6,277,141 B1 | * | 8/2001 | Lake |
| 6,436,126 B1 | * | 8/2002 | McAfee |

* cited by examiner

*Primary Examiner*—Michael A. Brown
*Assistant Examiner*—Fenn C Mathew
(74) *Attorney, Agent, or Firm*—Chambliss, Bahner & Stophel, P.C.

(57) ABSTRACT

The invention comprises a chiropractic table having a base, a plurality of frames, a plurality of drop mechanisms, and a plurality of cushions. The base has a longitudinal axis and the plurality of frames are attached to the base. Each frame has a first lateral side and a second lateral side which are substantially parallel to the longitudinal axis of the base. In addition, each frame has a pair of transverse sides which are substantially perpendicular to the first and second lateral sides. Each lateral side includes a frame hole. The frame holes in the first lateral side of each frame are substantially identically located with respect to the transverse side associated therewith, and the frame holes in the second lateral side of each frame are substantially identically located with respect to the transverse side associated therewith. The table is also provided with a plurality of cushions, each of which is adapted to be received by a frame. A plurality of fasteners for attaching the drop mechanisms to the frames are also provided. Each drop mechanism includes a housing which is adapted to be removably received within any of the frames for attachment to the lateral sides thereof. Each housing has a pair of mounting holes, each of which is adapted to align with a frame hole in the lateral side of a frame when the drop mechanism is received therein. Each of the plurality of fasteners may be passed through a mounting hole and a frame hole from outside the frame to attach the drop mechanism to the frame. A drop handle is pivotally connected to the drop mechanism and adapted for actuating the drop mechanism. The drop mechanism also includes a tension rod which is adapted to adjust the tension of drop mechanism. When the drop mechanism is mounted in the frame, the drop handle and the tension rod are positioned away from the frame.

9 Claims, 6 Drawing Sheets

MODULAR DROP MECHANISM FOR CHIROPRACTIC TABLE

FIELD OF INVENTION

This invention generally relates to modular drop mechanisms for use in chiropractic tables. More particularly, the invention relates to a method and apparatus for a chiropractic table assembly in which a plurality of modular drop mechanisms may be easily removed from and interchangeably replaced into frames in the chiropractic table from outside the frames.

BACKGROUND AND DESCRIPTION OF THE PRIOR ART

Chiropractic tables employing drop mechanisms are known for use in treating patients suffering from a variety of orthopedic and neuropathic maladies. Such tables are described in U.S. Pat. Nos. 4,523,581 and 5,954,750. Typically, chiropractic tables comprise a plurality of drop sections, each of which is directed at treating a particular part or parts of the patient's body. It is also common for chiropractic tables to utilize more than one drop mechanism in a particular drop section.

In conventional chiropractic tables, the different drop sections of the chiropractic table utilize different types of drop mechanisms, each of which is uniquely adapted for use in a particular section. In other words, the drop mechanism from one drop section of a chiropractic table may not be used in place of a drop mechanism from another drop section of the table. As a result, drop mechanisms cannot be interchangeably used in the different drop sections of a conventional chiropractic table.

Drop mechanisms utilized in conventional chiropractic tables are installed at the time of manufacture. Typically, the factory-installed drop mechanisms cannot be removed from or replaced into the chiropractic table in the field, e.g. in the doctor's office, without expending a great deal of time and effort. In fact, conventional chiropractic tables generally require significant modification of the table in order to permit removal and replacement of a drop mechanism, if it is even possible to do so in the field. Most chiropractic tables make removal and replacement of drop mechanisms impracticable. In those chiropractic tables that may be modified in the field, typically the drop system, the cocking system and the tensioning system are separate units which must be removed and replaced separately. As a result, conventional chiropractic tables have required the user to either undergo a difficult, time-consuming process to remove and replace drop mechanisms in the field or return the table to the factory. In either case, the chiropractic table cannot be utilized for significant periods of time, and patients cannot be treated for their ailments.

It would be desirable to provide a chiropractic table system with a drop mechanism which could be easily removed from and replaced into the chiropractic table in the field, e.g., in a doctor's office. It would be further desirable to provide a chiropractic table system with a drop mechanism which could be removed from and replaced into the chiropractic table without requiring any significant modification to the table. It would also be desirable to provide a chiropractic table system with drop mechanisms which could be interchangeably used in the different drop sections of the table. It would also be desirable to provide a chiropractic table in which the drop system, the cocking system and the tensioning system could be removed and replaced as an integral unit. It would also be desirable to provide a low-cost drop mechanism. It would also be desirable to provide a drop mechanism in which spare units could be maintained by a user and used to temporarily or permanently replace drop mechanisms requiring maintenance or repair.

Advantages of the Invention

Accordingly, it is an advantage of the invention that it provides a chiropractic table system in which the drop mechanisms may be easily removed from and replaced into the chiropractic table in the field. It is another advantage of the invention that it provides a chiropractic table system in which the drop mechanisms may be removed from and replaced into the chiropractic table without requiring significant modification to the table. It is yet another advantage of the invention that it provides a chiropractic table system in which a plurality of drop mechanisms may be interchangeably used in the different sections of the table. It is also an advantage of the invention that it provides a chiropractic table system in which the drop system, the cocking system and the tensioning system may be removed and replaced as an integral unit. It is also an advantage of the invention that it provides a low-cost drop mechanism. It yet another advantage of the invention that it provides a drop mechanism in which spare units may be maintained by a user, who can use the spare units to temporarily or permanently replace drop mechanisms requiring maintenance or repair.

Additional advantages of this invention will become apparent from an examination of the drawings and the ensuing description.

Explanation of Technical Terms

As used herein, the term "being positioned away from the frame" means being located either above or below the frame and not passing through the frame or any frame components.

SUMMARY OF THE INVENTION

The invention comprises a chiropractic table having modular drop mechanisms which can be easily removed and interchangeably replaced in the table without significantly modifying the table. According to the invention, the table comprises a base, a plurality of frames, a plurality of drop mechanisms, and a plurality of cushions. The base has a longitudinal axis, and the plurality of frames are attached to the base. Each frame has a first lateral side and a second lateral side which are substantially parallel to the longitudinal axis of the base. In addition, each frame has a pair of transverse sides which are substantially perpendicular to the first and second lateral sides. Each lateral side includes at least one frame hole. The frame holes in the first lateral side of each frame are substantially identically located with respect to the transverse sides associated therewith, and the frame holes in the second lateral side of each frame are substantially identically located with respect to the transverse sides associated therewith. The table is also provided with a plurality of cushions, each of which is adapted to be received by a frame. A plurality of fasteners for mounting the drop mechanisms to the frames are also provided.

Each drop mechanism includes a housing which is adapted to be removably received within any of the frames for attachment to the lateral sides thereof. Each housing has a pair of mounting holes, each of which is adapted to align with a frame hole in a lateral side of a frame when the drop mechanism is received therein. Each of the plurality of fasteners may be passed through a mounting hole and a frame hole from outside the frame to attach the drop mechanism to the frame. A drop handle is pivotally connected to the drop mechanism and adapted for actuating the drop mechanism. The drop mechanism also includes a tension rod which is adapted to adjust the tension of drop mechanism. When the drop mechanism is mounted in the frame, the drop handle and the tension rod are positioned away from the frame, i.e., either above or below the lateral sides of the frame.

The invention also comprises a method for removing, replacing and interchanging a modular drop mechanism in a chiropractic table having a base with a pair of frames attached thereto, a pair of drop mechanisms removably received in said frames, a pair of mounting fasteners for mounting the drop mechanisms in the frames, and a pair of cushions removably attached to said frames. The steps of the method include removing a pair of mounting fasteners from outside the frame, removing the drop mechanism from the frame, replacing the drop mechanism into any one of the frames, and replacing the pair of mounting fasteners from outside the frame.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
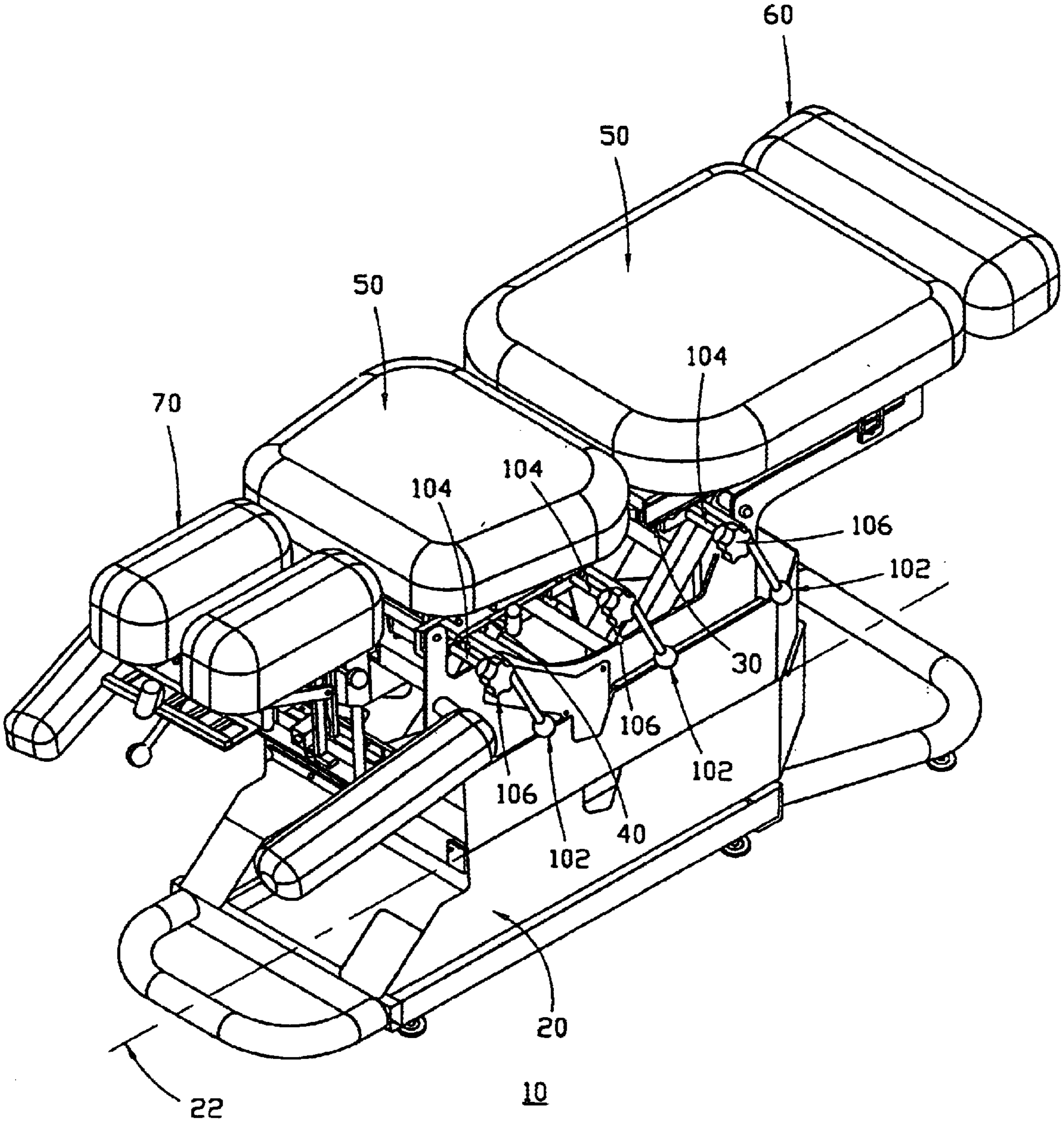
FIG. 1 is a perspective view of the chiropractic table of the invention.

Referring now to the drawings, the invention is illustrated by FIGS. 1 through 6. FIG. 1 illustrates a preferred embodiment of chiropractic table 10 in an assembled condition. Base 20 has a longitudinal axis 22 and provides support to pelvic frame 30 (See FIGS. 2–5), thoracic frame 40 (See FIGS. 2–5), drop mechanisms 100 (see FIGS. 2–6), and cushions 50. Pelvic frame 30 and thoracic frame 40 are attached to base 10 using conventional fastening means such as pivot rods 38 or bolts (not shown). Drop mechanisms 100 are removably mounted in pelvic frame 30 and thoracic frame 40 using fasteners 80 such as mounting bolts which may be removed and replaced from outside pelvic frame 30 and thoracic frame 40 (See FIGS. 2–5). Cushions 50 are removably received by pelvic frame 30 and thoracic frame 40 by conventional means. Also illustrated in FIG. 1 are drop handles 102, which are pivotally connected to and adapted for actuating drop mechanism 100, and tension rod 104, which is adapted to adjust the tension on drop mechanism 100. The opposing ends of tension rod 104 are provided with tension knobs 106, which are attached to tension rod 104 by conventional means. Foot assembly 60 is disposed at one end of table 10, and head assembly 70 is disposed at the opposite end of table 10.

Figure 2:
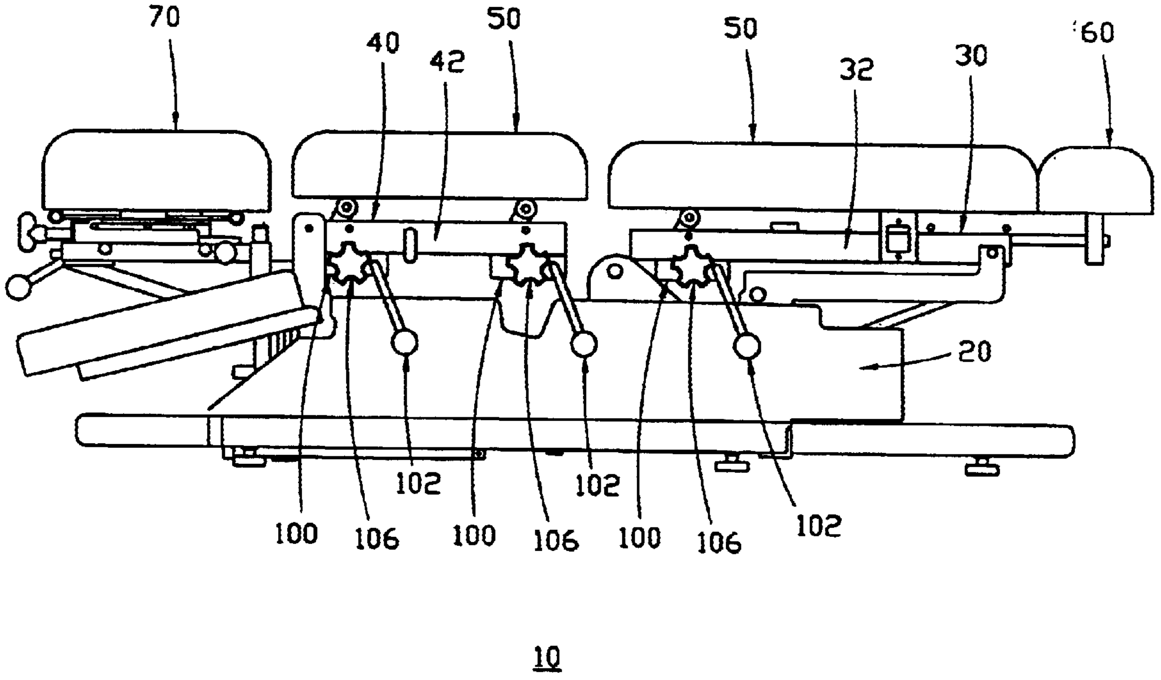
FIG. 2 is a perspective side view of the chiropractic table of FIG. 1.

FIG. 2 illustrates the side view of a preferred embodiment of the invention in an assembled condition. As shown in FIG. 2, base 20 provides support to pelvic frame 30 and thoracic frame 40, each of which is attached to base 20 using conventional means. Pelvic frame lateral side 32 and thoracic frame lateral side 42 are illustrated in FIG. 2. In addition, pelvic frame 30 and thoracic frame 40 support drop mechanisms 100, which are removably mounted in said frames using fasteners such as mounting bolts. Drop handles 102 and tension knobs 106 are positioned away from frames 30 and 40. In other words, they are located below lateral sides 32 and 42 when drop mechanism 100 is mounted in frames 30 and 40. Cushions 50 are removably received by pelvic frame 30 and thoracic frame 40 using conventional means. Foot assembly 60 and head assembly 70 are also supported by base 20.

Figure 3:
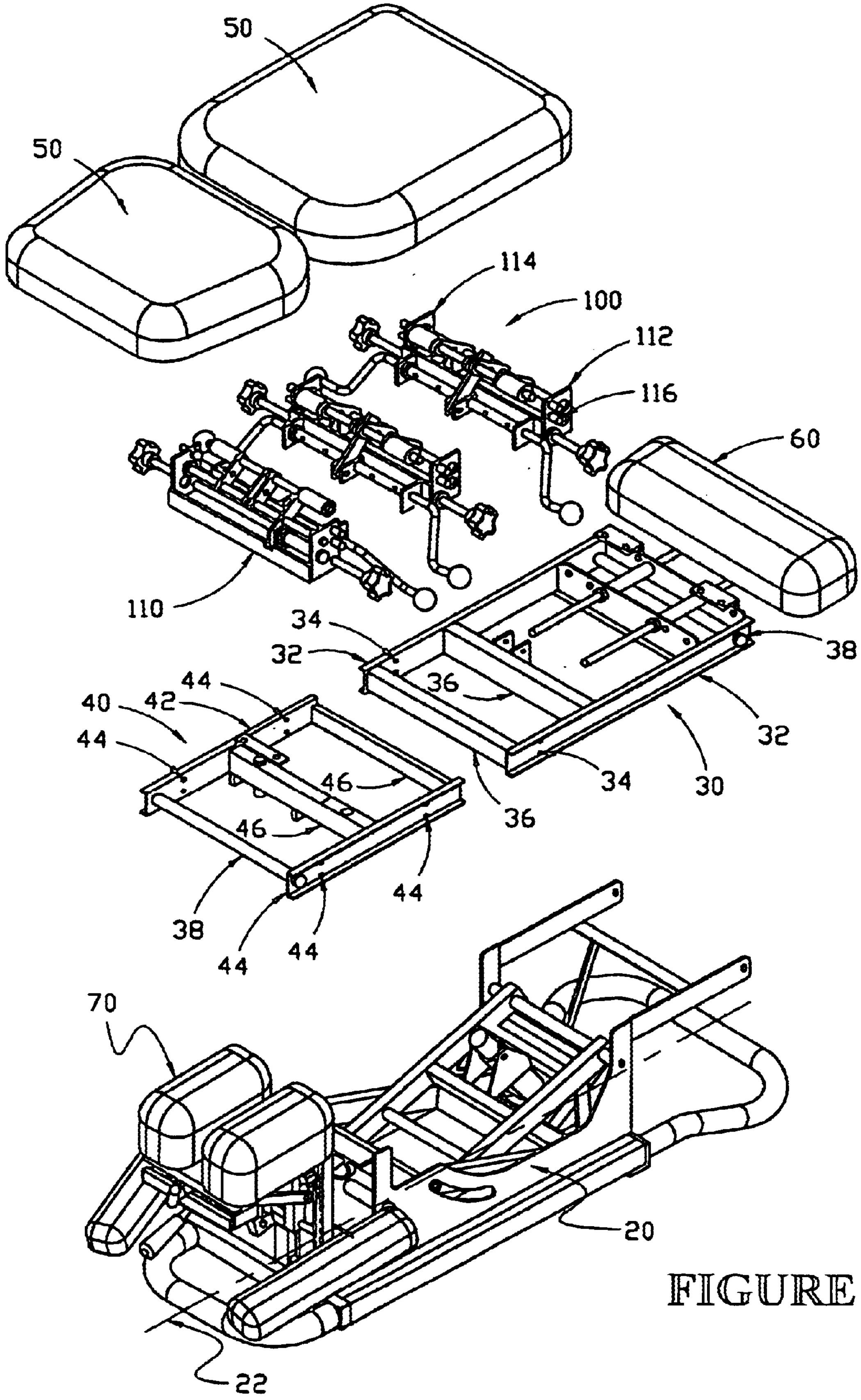
FIG. 3 is an exploded perspective view of the chiropractic table of FIGS. 1 and 2.

FIG. 3 illustrates the components of a preferred embodiment of the invention in a disassembled condition. Base 20 is generally disposed below pelvic frame 30, thoracic frame 40, drop mechanisms 100 and cushions 50 to provide support thereto. Pelvic frame 30 is disposed near foot assembly 60 and is adapted to removably receive one drop mechanism 100. Pelvic frame 30 comprises a pair of opposing pelvic frame lateral sides 32 which are substantially parallel to the longitudinal axis 22 of base 20. Each of the pelvic frame lateral sides 32 has at least one pelvic frame lateral side hole 34 which is adapted to receive a removable fastener 80 (See FIG. 4). The pelvic frame holes on each lateral side are substantially identically located with respect to the transverse sides associated therewith and adapted to align with mounting holes 116 in the lateral faces 112, 114 of housing 110 of the drop mechanism. When pelvic frame 30 is mounted on base 20, lateral side hole 34 is located such that it may be accessed from outside the frame. In addition, when pelvic frame 30 is mounted on base 20, fastener 80 may be removed from and replaced into pelvic frame lateral side hole 34 from outside the frame without any significant modification to base 20, frame 30, or drop mechanism 100. Pelvic frame 30 is also provided with a plurality of pelvic frame transverse sides 36 which are substantially perpendicular to the longitudinal axis 22 of base 20. Pelvic frame transverse sides 36 are adapted to provide support to pelvic frame lateral sides 32 and cushion 50. Pelvic frame transverse sides 36 are attached at their opposing ends to pelvic frame lateral sides 32. Pelvic frame lateral sides 32 and transverse sides 36 are adapted to removably receive a drop mechanism 100. Pelvic frame 30 may be mounted on base 20 using conventional means such as pivot rods 38 or bolts (not shown).

Thoracic frame 40 is disposed near head assembly 70 and is adapted to removably receive two drop mechanisms 100. Thoracic frame 40 comprises a pair of opposing thoracic frame lateral sides 42 which are substantially parallel to the longitudinal axis 22 of base 20. Each of the thoracic frame lateral sides 42 has least one thoracic frame lateral side hole 44 which is adapted to receive a removable fastener 80 (See FIG. 4). Thoracic frame holes in each lateral side are substantially identically located with respect to the transverse side associated therewith and adapted to align with mounting holes 116 in lateral faces 112 and 114 of housing 110 of the drop mechanism. When thoracic frame 40 is mounted on base 20, lateral side hole 44 is located such that it may be accessed from outside the frame. In addition, when thoracic frame 40 is mounted on base 20, fastener 80 may be removed from and replaced into thoracic frame lateral side hole 44 from outside the frame without any significant modification to base 20, frame 40, or drop mechanism 100. Thoracic frame 40 is also provided with a plurality of thoracic frame transverse sides 46 which are substantially perpendicular to the longitudinal axis 22 of base 20. Thoracic frame transverse sides 46 are attached at their opposing ends to thoracic frame lateral sides 42. Thoracic frame lateral sides 42 and transverse sides 46 are adapted to removably receive a drop mechanism 100. Thoracic frame 40 may be mounted on base 20 using conventional means such as bolts.

Figure 4:
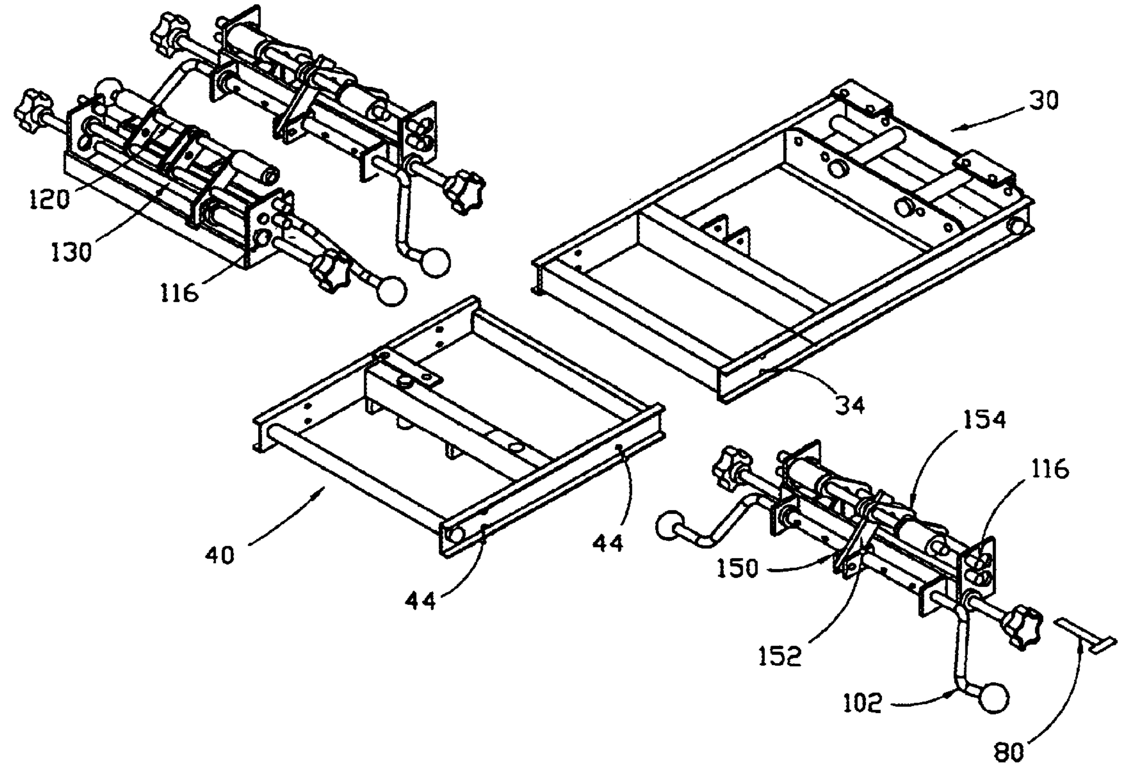
FIG. 4 is a perspective view of the thoracic frame, the pelvic frame and three drop mechanisms in a disassembled condition.
Figure 5:
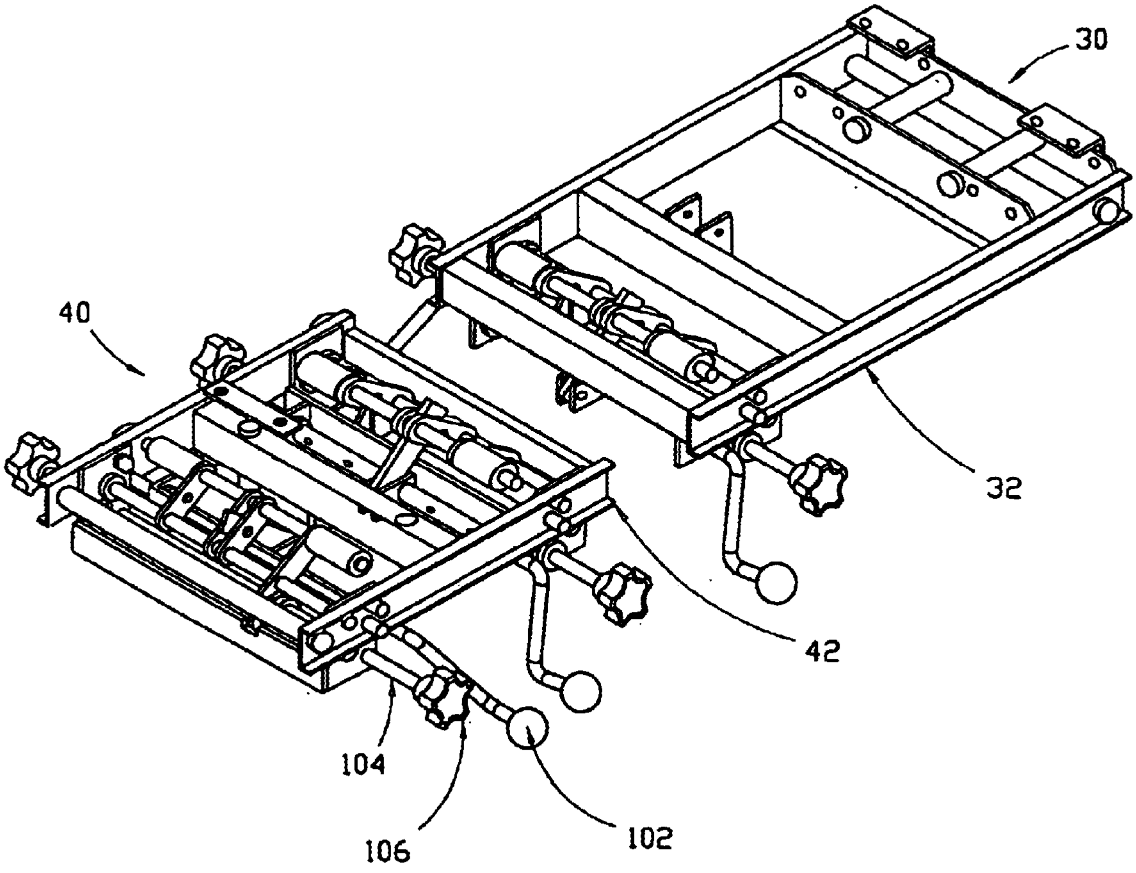
FIG. 5 is a perspective view of the components of FIG. 4 in an assembled condition.
Figure 6:
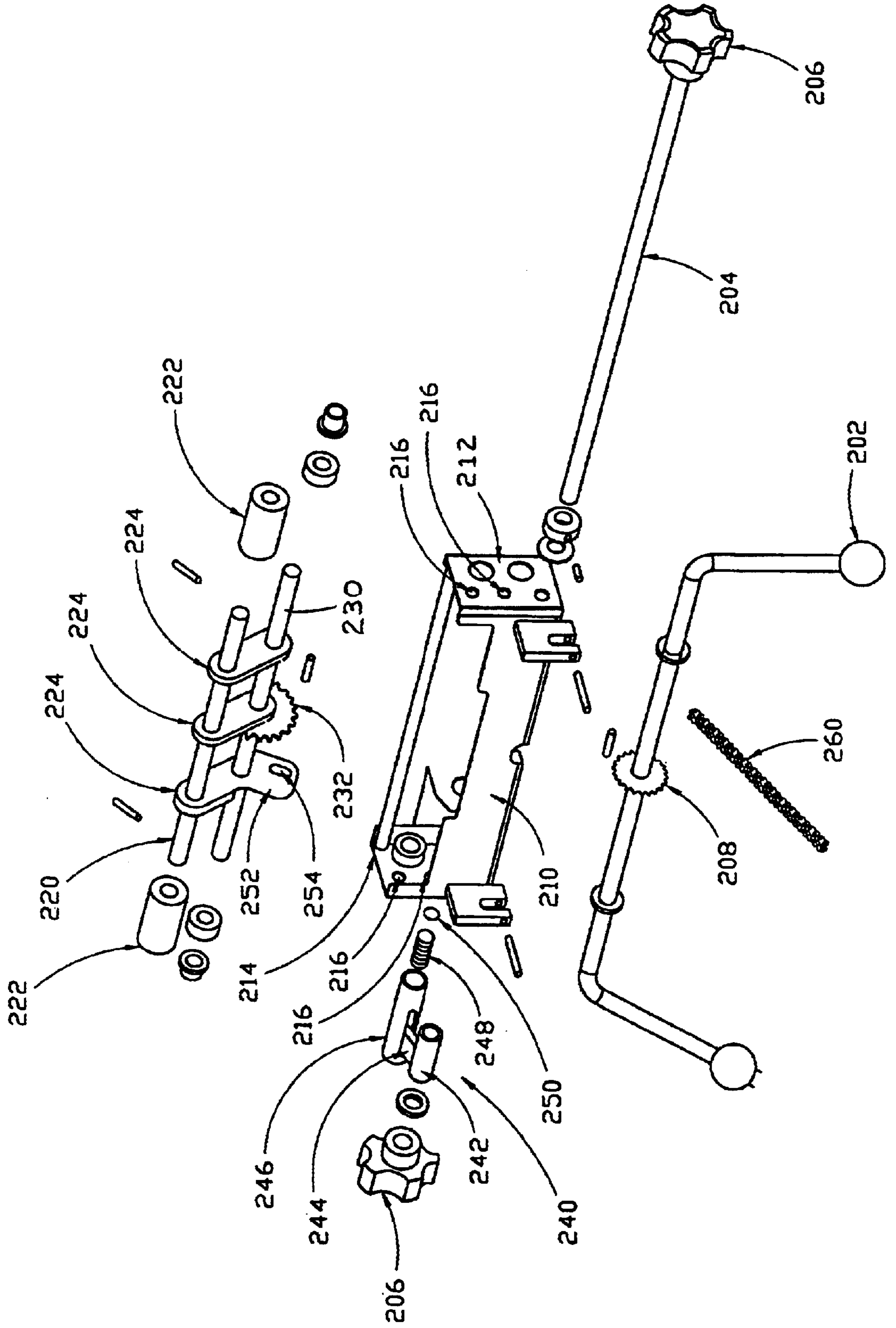
FIG. 6 is an exploded, perspective view of a preferred embodiment of the drop mechanism.

Drop mechanisms 100 are adapted to be interchangeably and removably received into pelvic frame 30 and thoracic frame 40, as illustrated in FIG. 5. The drop mechanisms 100 are also adapted to provide a drop apparatus, cocking apparatus and tensioning apparatus in a single, integral unit which may be replaced from and interchangeably replaced into frames 30 and 40. The drop mechanisms 100 illustrated in FIGS. 3 through 5 demonstrate one embodiment of a drop mechanism that is suitable for use in connection with the invention. FIG. 6 illustrates an alternative embodiment of the drop mechanism.

In the embodiment of the drop mechanism illustrated in FIGS. 3 through 5, drop mechanism 100, drop handle 102, first axle 120 and second axle 130 are connected by a conventional linking apparatus 150 (See FIG. 4). Linking apparatus 150 comprises a link 152 which is pivotally connected to drop handle 102 and center pin 154. Center pin 154 connects first axle 120 and second axle 130. Center pin 154 is adapted to slide along the groove (not shown) in link 152. It is also contemplated that the drop mechanism is actuated by a drop handle which is connected to the first or second axle by a fixed bracket (not shown) or a cam (not shown).

Referring now to FIG. 6, the alternative embodiment of the drop mechanism is generally designated as 200. Drop mechanism 200 comprises drop handle 202, housing 210, first axle 220, second axle 230, and tension adjusting apparatus 240. Housing 210 generally provides support to the components of drop mechanism 200. Drop handle 202 is pivotally connected to housing 210 and adapted to actuate the drop mechanism. Drop handle 202 includes handle sprocket 208 which is adapted to receive chain 260.

Tension rod adjusting apparatus 240 is adapted to adjust the tension on the drop mechanism by conventional means. Tension rod adjusting means comprises threaded tension rod 204, which is rotatably connected to housing 210 and tension rod knobs 206, which are attached to rod 204 at opposite ends thereof. Tension adjustment apparatus 240 also includes bushing 242, metal finger 244, spring tube 246, compressive spring 248, ball bearing 250, striker plate 252 and recess hole 254. Threaded tension rod 204 is adapted to fit into bushing 242, which is provided with metal finger 244. Metal finger 244 fits into spring tube 246 and is adapted to bear against compressive spring 248 which is substantially contained in tube 246. Compressive spring 248 bears against and exerts force upon ball bearing 250 which is adapted to seat in, but not pass through, recess hole 254 in striker plate 252 when the drop mechanism is cocked. When the drop mechanism is released, ball bearing 250 moves from a seated position in recess hole 254 and rotates along a ramp (not shown). Drop handle 202 and tension rod 204 are located below the lateral sides of pelvic frame 30 and thoracic frame 40 when drop mechanism 200 is mounted in frame 30 or frame 40.

Second axle 230 is pivotally connected to housing 210 in a position substantially perpendicular to the longitudinal axis 22 of base 20. Second axle 230 includes sprocket 232 which is adapted to receive chain 260. Second axle 230 is attached to first axle 220 using a plurality of plates 224. First axle 220 is substantially parallel to second axle 230. First axle 220 is provided with a plurality of rollers 222 which are adapted to bear against cushions 50. Chain 260 connects axle sprocket 232 and handle sprocket 208.

Housing 210 has opposing lateral faces 212 and 214 which are substantially coplanar with the lateral sides of the pelvic and thoracic frames when the drop mechanism is mounted in frames 30 and 40. A plurality of mounting holes 216 are located in the lateral faces 212 and of housing 210. Mounting holes 216 on lateral face 212 are substantially identically located to the mounting holes on lateral face 214. Mounting holes 216 are also located such that they align with pelvic frame lateral side holes 34 and thoracic frame lateral side holes 44. While FIG. 6 illustrates two mounting holes in each lateral face of housing 210, it is understood that the invention may be accomplished using only one mounting hole 216, or more than two, in each lateral face of housing 210.

In operation, the drop mechanism is actuated by lifting the drop handle. When the drop handle is lifted, it pivots with respect to the housing causing the drop handle sprocket to rotate. When the drop handle sprocket is rotated, the chain moves with the sprocket and causes the second axle sprocket to rotate. When the second axle sprocket rotates, the second axle also rotates with respect to the housing. The rotation of the second axle causes the first axle to move in a direction toward the cushion associated therewith. This rotation causes the striker plate to rotate, thereby aligning the recess hole in the plate with the ball bearing. The ball bearing, which is spring biased, seats in the recess hole. The drop mechanism is now in the cocked position. The amount of force required to unseat the ball bearing from the recess hole is determined by the user through the tension adjusting apparatus. The threaded tension rod may be rotated using the tension knobs to increase or decreased the force exerted on the striker plate by the ball bearing through the compressive spring. When the required downward force is placed on the cushion, the ball bearing unseats from the recess hole, thereby allowing the rollers to rotate away from the cushion. As the first axle moves away from the cushion, the rollers rotate along the bottom surface of the cushion allowing the cushion to drop.

Moreover, the drop mechanisms may be removed from the pelvic and thoracic frames and interchangeably replaced into them by simply removing and replacing the mounting bolts from outside the frame. The mounting bolts may be accessed from outside the frame without any significant modification to the drop mechanisms, the frames or the base. The drop mechanisms may be removed and replaced by simply removing and replacing the mounting bolts from outside the frame and sliding the drop mechanism under the frames from either side of the table. Unlike other chiropractic tables, the drop mechanisms in this invention may be removed and replaced in the field without returning the table to the factory. Also unlike other chiropractic tables, the drop mechanisms in this invention may be interchangeably used in any of the frames in the table.

Although this description contains many specifics, these should not be construed as limiting the scope of the invention but merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A chiropractic table which comprises:

(a) a base having a longitudinal axis;

(b) a plurality of frames attached to the base, each frame having:

(i) a first lateral side which is substantially parallel to the longitudinal axis;

(ii) a second lateral side which is substantially parallel to the longitudinal axis;

(iii) a pair of transverse sides which are substantially perpendicular to the first and second lateral sides; and (iv) a frame hole in each of the lateral sides;

wherein the frame holes in the first lateral side of each frame are substantially identically located with respect to the transverse sides associated therewith and the frames hole in the second lateral side of each frame are substantially identically located with respect to the transverse sides associated therewith;

(c) a plurality of cushions, each of which is adapted to be received by a frame;

(d) a plurality of fasteners; and (e) a plurality of drop mechanisms, each of which has:

(i) a housing which is adapted to be removably received within any of the frames for attachment to the lateral sides thereof, said housing having a pair of mounting holes, each of which is adapted to align with a frame hole in the lateral side of a frame when the drop mechanism is received therein so that a fastener may be passed through the mounting hole and the frame hole from outside the frame to attach the drop mechanism to the frame;

(ii) a drop handle pivotally connected thereto and adapted for actuating the drop mechanism, said drop handle being positioned away from the frame when the drop mechanism is mounted therein;

(iii) a tension rod that is adapted for adjusting the drop mechanism, said tension rod being positioned away from the frame when the drop mechanism is mounted therein.

2. The chiropractic table of claim 1 wherein the drop handle is positioned below the frame when the drop mechanism is mounted in the frame.

3. The chiropractic table of claim 1 wherein the tension knob is positioned below the frame when the drop mechanism is mounted in the frame.

4. The chiropractic table of claim 1 wherein the plurality of fasteners are mounting bolts.

5. The chiropractic table of claim 1 wherein each of the plurality of drop mechanisms further comprises:

(iv) a first axle having a plurality of rollers;

(v) a second axle being connected to said first axle by a plurality of plates such that the first axle and the second axle are substantially perpendicular to the longitudinal axis of the base; and, (vi) a link for connecting the second axle and the drop handle.

6. The chiropractic table of claim 1 wherein each of the plurality of drop mechanisms further comprises:

(iv) a first axle having a plurality of rollers;

(v) a second axle being connected to said first axle by a plurality of plates such that the first axle and the second axle are substantially perpendicular to the longitudinal axis of the base; and, (vi) a bracket for connecting the second axle and the drop handle.

7. A chiropractic table which comprises:

(a) a base having a longitudinal axis;

(b) a plurality of frames attached to the base, each frame having:

(i) a first lateral side which is substantially parallel to the longitudinal axis of the base;

(ii) a second lateral side which is substantially parallel to the longitudinal axis of the base;

(iii) a pair of transverse sides which are substantially perpendicular to the longitudinal axis of the base and connected to the lateral sides;

(iv) a frame hole in each of the lateral sides;

wherein the frame holes in the first lateral side of each frame are substantially identically located with respect to the transverse sides associated therewith, and the frame holes in the second lateral side of each frame are substantially identically located with respect to the transverse sides associated therewith;

(c) a plurality of cushions, each of which is adapted to be received by a frame;

(d) a plurality of mounting bolts;

(b) a plurality of drop mechanisms, each having:

(i) a housing which is adapted to be removably received within any of the frames for attachment to the lateral sides thereof, said housing having a pair of mounting holes, each of which is adapted to align with a frame hole in the lateral side of a frame when the drop mechanism is received therein so that a mounting bolt may be passed through the mounting hole and the frame hole from outside the frame to attach the drop mechanism to the frame;

(ii) a first axle having a plurality of rollers;

(iii) a second axle having an axle sprocket;

(iv) a drop handle adapted for actuating the drop mechanism and having a handle sprocket, said drop handle being pivotally connected to the housing and being positioned away from the frame when the drop mechanism is mounted therein;

(v) a chain for connecting the axle sprocket and the handle sprocket;

(vi) a plurality of plates connecting the first axle and the second axle such that the first axle and the second axle are substantially perpendicular to the longitudinal axis of the base;

(vii) a tension rod that is adapted for adjusting the drop mechanism, said tension rod being positioned away from the frame when the drop mechanism is mounted therein.

8. The chiropractic table of claim 7 wherein the drop handle is positioned below the frame when the drop mechanism is mounted in the frame.

9. The chiropractic table of claim 7 wherein the tension rod is positioned below the frame when the drop mechanism is mounted in the frame.

* * * * *